United States Patent [19]

Bachmann

[11] Patent Number: 4,950,655

[45] Date of Patent: Aug. 21, 1990

[54] COMPOSITION FOR TREATING AND PREVENTING DIARRHOEA IN HUMANS AND ANIMALS AND A METHOD OF PREPARING SAME

[76] Inventor: Poul Bachmann, Demstrupvej 31, DK-8900 Randers, Denmark

[21] Appl. No.: 67,303
[22] PCT Filed: Oct. 14, 1986
[86] PCT No.: PCT/DK86/00116
§ 371 Date: Jun. 12, 1987
§ 102(e) Date: Jun. 12, 1987
[87] PCT Pub. No.: WO87/02243
PCT Pub. Date: Apr. 23, 1987
[51] Int. Cl.$^5$ .................... A61K 31/00; A61K 37/00; C08B 37/00
[52] U.S. Cl. .................... 514/54; 514/867; 536/2
[58] Field of Search .................... 514/54, 867; 536/2

[56] References Cited

U.S. PATENT DOCUMENTS

| | | | |
|---|---|---|---|
| 2,139,139 | 12/1938 | Tompkins | 514/54 |
| 2,145,016 | 1/1939 | Spalding | 514/54 |
| 2,333,950 | 11/1943 | Olsen et al. | 424/180 |
| 3,928,574 | 12/1975 | Phillips | 514/867 |
| 4,162,306 | 7/1979 | Laves | 424/125 |
| 4,443,467 | 4/1984 | Ward | 514/256 |
| 4,684,632 | 8/1987 | Schulz et al. | 514/926 |

FOREIGN PATENT DOCUMENTS

| | | |
|---|---|---|
| 1214393 | 11/1986 | Canada. |
| 0059057 | 9/1982 | European Pat. Off. ........... 424/330 |
| 0147741 | 12/1985 | European Pat. Off. . |
| 0174006 | 3/1986 | European Pat. Off. . |
| 2715384 | 10/1981 | Fed. Rep. of Germany. |
| 2566664 | 1/1986 | France. |
| 1182463 | 5/1968 | United Kingdom. |
| 1380292 | 1/1975 | United Kingdom. |

OTHER PUBLICATIONS

Berkeley et al., Editors, "Microbial Adhesion to Surfaces" Ellis Horwood Limited, Publisher, Sect. 28.13, pp. 537–538.

Primary Examiner—Ronald W. Griffin
Assistant Examiner—Everett White
Attorney, Agent, or Firm—Irell & Manella

[57] ABSTRACT

A composition for treating and preventing diarrhoea in humans and animals comprising a pectinaceous material and an amphophilic substance which is resistant to decomposition under the conditions prevailing in the stomach, and which contains a long-chained hydrophobic group. The use of the amphophilic substance significantly increases the curing and prophylactic effect of the pectinaceous material on diarrhoea.

11 Claims, No Drawings

COMPOSITION FOR TREATING AND PREVENTING DIARRHOEA IN HUMANS AND ANIMALS AND A METHOD OF PREPARING SAME

This invention relates to a composition for treating and preventing diarrhoea in humans and animals, said composition comprising a pectinaceous material and an additive for increasing the effect of the pectinaceous material.

It has long been known to use pectinaceous preparations for the treatment of diarrhoea in humans and in particular infants, cf. DE patent specification No. 720.948.

GB patent specification No. 1.380.292 discloses a pectinaceous feed additive containing pectin and an additive for increasing the amount of acid of the stomach contents, said additive serving to accelerate the conversion of protopecin into physiologically active pectin and thus to improve the effect of pectin on diarrhoea.

Furthermore, GB patent specification No. 1.182.463 discloses a pharmaceutical composition for the treatment of diarrhoea and other gastric and intestinal disorders, said composition containing absorbent aluminium silicate and a glyceride of a saturated aliphatic carboxylic acid and optionally lecithin which serves to give the composition a smoother, finer but crystalline structure.

EP patent publication N. 0 021 230 A2 discloses a composition for treating or preventing infections in human being and animals. The composition comprises one or more polymeric carbohydrates or sugar alcohols having a hydrophobic group and a molecular weight which is sufficiently high to prevent it from penetrating a cellular membrane and a physiologically acceptable water-insoluble inorganic material exhibiting a hydrophobic surface layer. The purpose of using said combination of a polymer having a hydrophobic group and an inorganic material exhibiting a hydrophobic surface layer is to attract patogenic bacteria and to cause the bacteria to adhere to the polymer and the inorganic material rather than the cell tissue, e.g. the intestinal cell tissue. The composition does not contain pectin and the introduction of the hydrophobic group on the polymer is based on a chemical reaction, viz. an etherification, esterificattion or amidation.

DK patent application No. 2719/84 discloses a dietary fiber product which is readily dispersible in water and which consists of 80-99.95% by weight of dietary fibres and 0.05-20% by weight of an emulsifier, e.g. lecithin. The dietary fibres used are psyllium powder, bran, cellulosic derivatives, malt extract, wheat sprouts etc. The dietary fibre product is mainly used as a laxative.

The mechanisms which are responsible for diarrhoea have not been fully elucidated. As far as the most widespread diarrhoea based on infections is concerned, recent research seems to indicate that several of these disorders (Salmonellose, *Escherichia coli* diarrhoea and *Vibro cholerate* diarrhoea) are due to the adhesion of specific pathogenic bacteria strains to the mucous membrane of the small intestine. This phenomenon is normally called bacteria colonisation.

Bacterial adhesion to the mucous membrane of the intestines occurs in two forms:

(1) A reversible "adhesion" caused by non-specific pili extending from the surface of the bacteria cells (for *Eschericia coli*: Type+1 fimbriae).

(2) An non-reversible adherence which is accompanied by a bacterial propagation and which is caused by the presence of specific antigenic formations on the surface of the bacterial capsula (antigenic pili).

It should be pointed out that only the non-reversible adherence mentioned sub (2) is of pathogenic significance becaus of the development of an actual colonisation.

Due to the secretion of mucus, a permanent renewal of epithel and supply of bile to the small intestine as well as the peristalic movements of the small intestine etc., the bacterial flora is rather sparse with the exception of a high number of lacto bacteria. The number of *Escherichia coli* (E. coli) in the anterior end of the small intestine in normal pigs is $10^3$–$10^4$ per g of the contents of the small intestine, whereas this number in cases of diarrhoea associated with *E. coli* is $10^9$ bacteria per g.

The pathogenesis in infections associated with *E. coli* comprises the following steps: Infection (orally) with patogenic *E. coli* strains, colonisation of the mucous membranes of the small intestine, propagation in the small intestine and formation of toxin.

Recent investigations show that enteropathogenic *E. coli* colonize the villus of the intestines by adhesion, whereas nonpathogenic bacteria neither adhere to nor colonize these villi.

The colonisation of the mucous membrane of the small intestine is followed by a propagation and during the latter the number of intimately adhering bacteria is strongly increased, e.g. with a factor of $10^3$–$10^4$.

The pathogenic bacteria adhering to the mucous membrane produce enterotoxine and these toxines are responsible for the occurrence of diarrhoea by causing liquid to migrate from the mucous membrane to the lumen of the intestine.

It has been found that the ability of the pathogenic bacteria to adhere to the mucous membrane of the small intestine is important for the development of diarrhoea and that this property is associated with the surface structure of the bacterial cells. This structure can have the form of thread-like structures of a proteinaceous type and these structures are called fimbriae, fibrillae and pili.

It is assumed that pectin influences the ability of the diarrhoea producing bacteria to adhere to the mucous membrane by attracting and retaining the bacteria cells, thus preventing them from adhering to the mucous membrane. This effect seems to be associated with the ability of pectin to form a gel which is due to the fact that the galacturonic acid chains of pectin are distinctly hydrophilic.

The invention is based on the discovery that lecithins are capable of significantly improving the ability of attracting and retaining bacteria cells of pectinaceous products.

This is supported by some laboratory tests which have been carried out with products consisting of pectin fibres and lecithin and similar well known pectinaceous products containing no lecithin.

In these laboratory tests the capability of pectinaceous products with respect to the binding of strains of diarrhoea producing bacteria was determined by hydrophobic interaction chromatography (HIC). In this method a known amount of the pectinaceous product to be investigated is applied to a column of Octyl-Sepharose ®, and a known amount of pathogenic bacteria is then supplied to the column. After washing the column with a buffer, the eluate is subjected to a spectrophotometric determination to determine the amount of bacteria retained on the column.

The following results were obtained in these laboratory tests:

TABLE 1

| | Bacteria strain | Retention, %, average value |
|---|---|---|
| 1st Test Run: | | |
| Citrus pectin fibres | E. coli K88 No. 221 | 74.0 |
| Citrus pectin fibres + lecithin | " | 90.1 |
| Potato pectin fibres | " | 54.5 |
| Potato pectin fibres + lecithin | " | 76.3 |
| 2nd Test Run: | | |
| Citrus pectin fibres | S. dublin Li | 46.5 |
| Citrus pectin fibres + lecithin | " | 97.5 |
| 3rd Test Run: | | |
| Citrus pectin fibres | E. coli No. 221 | 26.8 |
| Citrus pectin fibres + lecithin | " | 57.8 |
| 4th Test Run: | | |
| Citrus pectin fibres | S. dublin li | 24.0 |
| Citrus pectin fibres + lecithin | " | 96.7 |

As will appear from these test results, a distinct increase of the retention of the above mentioned bacteria was obtained by addin lecithin to the pectin fibres.

Similar results have been obtained by tests with 199 calves suffering from diarrhoea. The calves which were part of stocks which had been selected as representatives for Danish agriculture were treated 3 times daily with 70 g of a mixture having the composition set forth in example 1 below and slurried in 2 liters of water for a period of 1-2 days.

During the treatment 197 calves were cured, whereas 2 remained unhealthy or dried. In view of the fact that experience shows that about 20% of diarrhoea-stricken calves which are treated with a non-modified pectinaceous feed additive die, the test clearly shows that lecithin distinctly improves the effect of pectin on diarrhoea.

Lecithins are glycerol esters in which two of the hydroxy groups of glycerol have been esterified with fatty acids, the fatty acids of animal lecithins mainly being stearic acid and in vegetable lecithins mainly being oleic acid and palmitic acid, and in which the third hydroxy group has been esterified with phosphoric acid which has been esterified with a N-containing base, such as choline.

Lecithins are amphophilic compounds because the same molecule contains both a hydrophobic (lipophilic) group, viz. a long hydrocarbon group, as well as a hydrophilic group, viz. a phosphate and ammonium group.

It is well known that the above mentioned surface structures on bacteria which are called pili contain antigens (adhesins) which specifically are bonded to specific host cells and which contain a large number of hydrophobic non-polar amino acid residues. The latter are believed to be responsible for the hydrophobicity which appears to be decisive for the adhesion of the pathogenic bacteria to the epithel of the intestines.

Recent investigations, cf. Microbial Adhesion to Surfaces, edited by R. C. W. Berkeley, J. M. Lynch, J. Melling, P. R. Rutter and B. Vincent, pages 337–540, show that the inclination of bacteria for being bonded to gels, such as Sepharose ®-gel substituted with aliphatic chains increase with increasing hydrophobicity, i.e. with increasing chain length of the aliphatic chains.

Since pectins as mentioned above form gels and since lecithin apparently imparts to pectin gels an increased hydrophobicity which presumably is due to the relatively long fatty acid residues in lecithin, it is reasonable to assume that also other amphophilic compounds than lecithin and having a relatively long hydrophobic group have a favourable effect on the ability of pectin to bind bacteria.

This assumption has been supported by tests which have been carried out with two commercially available amphophilic substances, viz. an ester A having the formula:

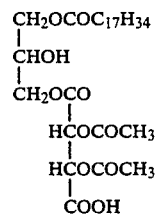

and a mixture, B, of mono, di and triglycerides of oleic acid.

in these tests the above mentioned 4th test run was extended to comprise a mixture of citrus pectin fibres and compound A and a mixture of citrus pectin fibres and mixture B. The result of these tests are shown in the following table 2.

TABLE 2

| | Bacteria strain | Retention, %, average value |
|---|---|---|
| Citrus pectin fibres + compound A | S. dublin li | 75.7 |
| Citrus pectin fibres + mixture B | " | 56.3 |

As will appear from these results, the bacteria retention of the two mixtures is much higher than for citrus pectin fibres alone (cf. table 1).

A necessary condition for improving the ability of pectin to bind bacteria by means of an additive is of course that the additive is not decomposed in the stomach.

Thus, the invention is characterized in that the additive at least partially is constituted by an amphophilic substance which is resistant to decomposition under the conditions prevailing in the stomach and which contains at least one long-chained hydrophobic group.

A preferred group of amphophilic substances for use in the composition according to the invention is glycerol esters and particularly lecithins. A particularly preferred lecithin is soy lecithin.

Examples of long-chained hydrophobic groups are straight-chained or branched saturated or unsaturated aliphatic, alicyclic or aromatic groups. The long-chained hydrophobic group can optionally be substituted, for example with one or more halogen atoms or alkoxy groups, and may optionally contain oxygen or sulphur atoms.

The term "long-chained" means that the number of carbon atoms is at least 12.

The term "pectinaceous material" means both pure pectin and products containing pectin in admixture with other components. Paticularly preferred are pectin fibres. The pectinaceous material may be obtained from various sources but preferred sources are citrus fruits, potatos and apples.

The weight ratio of pectin to amphophilic substance is preferably from 1:1 to 50:1 and more preferred from 2:1 to 3:1.

Depending on the desired use, the composition of the invention may contain other components than pectinaceous material and amphophilic substance.

E.g. the composition can contain electrolytes, such as sodium chloride and sodium carbonate and glucose and optionally an anti-caking composition, such as finely divided silicium oxide.

The invention also relates to a method of preparing the above mentioned composition. This method comprises admixing the pectinaceous material and the amphophilic substance and optionally drying the mixture thus obtained. The pectinaceous starting material may be wet pectin pulp or dry milled pectinaceous material. When using a dry pectinaceous material, it is preferably mixed with an anti-caking composition before admixture with the amphophilic substance.

The invention will now be described in further detail with reference to the following examples.

EXAMPLE 1

A food supplement of the following composition:

| | |
|---|---|
| Pectin fibres | 32.5% by weight |
| Soy lecithin | 13.0% by weight |
| Electrolytes: | |
| NaCl | 5.5 by weight |
| $Na_2CO_3$ | 10.8% by weight |
| Glucose | 32.2% by weight |
| Finely divided $SiO_2$ | 6.0% by weight |
| Total | 100.0% by weight | is prepared in the following manner:

325 kg dried, milled pectinaceous citrus fibres containing 10-14% of water and having an average particle size of 0.5 mm are introduced into a stainless horizontal mixer having a volume of 1500 liters and comprises means for varying the mixing rate. 130 kg soy lecithin are heated to about 70° C. and are then slowly sprayed onto the citrus fibres during slow stirring. Subsequently, 322 kg glucose and 63 kg electrolytes are added and the mixture is slowly stirred for 30 minutes. Finely divided $SiO_2$ is added under vigorous stirring, and a final mixing is effected for 15 minutes at the highest mixing rate.

The composition is dispensed together with lukewarm water in a weight ratio of 0.035 parts by weight of food supplement per part by weight of water.

EXAMPLE 2

The following mixture:

| | |
|---|---|
| Pectin fibres | 52.0% by weight |
| Soy lecithin | 30.0% by weight |
| Finely divided $SiO_2$ | 18.0% by weight |
| Total | 100.0% by weight | is prepared in the same manner as in example 1. It is mixed with fodder in an amount of 1-10%.

EXAMPLE 3

A mixture having the same composition as that of example 2 is prepared by spraying the citrus fibres with liquid soy lecithin and subsequently powdering with finely divided $SiO_2$ in a spraymix plant comprising a fluid bed. The composition may be used in the same manner as the mixture according to example 2 or can be mixed with electrolytes and glucose and used in the same manner as the mixture according to example 1.

EXAMPLE 4

Plastic, unbleached soy lecithin (a by-product obtained by soy oil extraction) is added to a citrus pulp (disintegrated fruit residue) obtained directly from the fruit press.

The citrus pulp used has a dry matter content of 12-15%, the galacturonic acid polymers (pure pectin) constituting 18-25%, and a pH value of 5.0-5.5. The pulp had not been treated with added calcium which is used under certain circumstances in order to increase the release of water during the pressing operation or polygalacturonases which are pectin-digesting enzymes which in some cases are used for juice clarification.

By intimate mechanical stirring the two components are mixed to form a homogenous mixture having an emulsion-like character which is evidenced by a slight bleaching and a slightly fatty texture.

The lecithin is used in an amount of 50% by weight of the pectin.

The mixture thus prepared is left to stand for at least 15 hours, whereafter it is dried to a dry matter content of 85-88% at a maximum temperature of 80° C.

The dried product is milled to an average particle size of 0.5 mm.

The mixture can be used in the same manner as the mixture according to example 2 or mixed with electrolytes and glucose and used in the same manner as the mixture according to example 1.

EXAMPLE 5

Potato pulp obtained directly from a potato starch factory is mixed with soy lecithin in a concentration of 4-5% relative to the contents of galacturonate.

The mixture is processed in the same manner as described in example 1.

It is pointed out that the contents of galacturonase in potato pulp falls drastically during the harvest season (from the middle of August to the end of December).

I claim:

1. A composition for treating and preventing diarrhoea in humans and animals, said composition comprising a pectinaceous material and an effective amount of an additive effective in increasing the effect of the pectinaceous material in binding bacteria capable of causing said diarrhoea,
    wherein said additive is an amphophilic glycerol ester of at least one hydrophobic long chain (>12C) carboxylic acid which is resistant to decomposition under the conditions prevailing in the stomach.

2. A composition according to claim 1 wherein the additive is lecithin.

3. A composition according to claim 2 wherein the ratio of pectinaceous material to additive is from 1:1 to 50:1.

4. A composition according to claim 2 which further contains an electrolyte mixture or glucose or a mixture thereof.

5. A composition according to claim 2 which further contains an anti-caking composition.

6. A composition according to claim 1 wherein the ratio of pectinaceous material to additive is from 1:1 to 50:1.

7. A composition according to claim 6 which further contains an electrolyte mixture or glucose or a mixture thereof.

8. A composition according to claim 6 which further contains an anti-caking composition.

9. A composition according to claim 1 which further contains an electrolyte mixture or glucose or a mixture thereof.

10. A composition according to claim 9 which further contains an anti-caking composition.

11. A composition according to claim 1 which further contains an anti-caking composition.

* * * * *